United States Patent
Yao et al.

(10) Patent No.: US 10,920,206 B2
(45) Date of Patent: Feb. 16, 2021

(54) ACIDIC THERMOPHILIC POLYGALACTURONASE TEPG28A, AND ENCODING GENE AND APPLICATION THEREOF

(71) Applicant: FEED RESEARCH INSTITUTE, CHINESE ACADEMY OF AGRICULTURAL SCIENCES, Beijing (CN)

(72) Inventors: Bin Yao, Beijing (CN); Huiying Luo, Beijing (CN); Yeqing Li, Beijing (CN); Yuan Wang, Beijing (CN); Tao Tu, Beijing (CN); Huoqing Huang, Beijing (CN); Yingguo Bai, Beijing (CN); Yaru Wang, Beijing (CN); Xiaoyun Su, Beijing (CN)

(73) Assignee: FEED RESEARCH INSTITUTE, CHINESE ACADEMY OF Agricultural Sciences, Beijing (CN)

( * ) Notice: Subject to any disclaimer, the term of this patent is extended or adjusted under 35 U.S.C. 154(b) by 0 days.

(21) Appl. No.: 16/344,699

(22) PCT Filed: Dec. 15, 2016

(86) PCT No.: PCT/CN2016/110207
§ 371 (c)(1),
(2) Date: Apr. 24, 2019

(87) PCT Pub. No.: WO2018/076496
PCT Pub. Date: May 3, 2018

(65) Prior Publication Data
US 2020/0199557 A1 Jun. 25, 2020

(30) Foreign Application Priority Data

Oct. 28, 2016 (CN) .......................... 2016 1 0959048

(51) Int. Cl.
*C12N 9/24* (2006.01)
*C12P 19/14* (2006.01)
*C12N 15/81* (2006.01)

(52) U.S. Cl.
CPC ......... *C12N 9/2402* (2013.01); *C12N 15/815* (2013.01); *C12Y 302/01015* (2013.01)

(58) Field of Classification Search
None
See application file for complete search history.

(56) References Cited

U.S. PATENT DOCUMENTS

2010/0192985 A1* 8/2010 Aehle ................ C11D 3/38609
134/26

FOREIGN PATENT DOCUMENTS

WO   WO-2014059541 A1 * 4/2014 ............... C12N 9/24

OTHER PUBLICATIONS

Sang, H., Mech. Dev., 121:1179-1186, 2004 (Year: 2004).*
Goswami et al., Front. Onc. 9:297, 2019, 25 pages (Year: 2019).*
Zhang et al., Structure 26:1474-1485, 2018 (Year: 2018).*
Fernandes et al., "Enzyme Systems From the Thermophilic Fungus *Talaromyces emersonii* for Sugar Beet Bioconversion", BioResources 3:898-909, 2008 (Year: 2008).*
Li et al., "Two acidic, thermophilic GH28 polygalacturonases from Talaromyces leycettanus JCM 12802 with application potentials for grape juice clarification", Food Chem. 237:997-1003, 2017 (Year: 2017).*

* cited by examiner

*Primary Examiner* — David Steadman
(74) *Attorney, Agent, or Firm* — Patshegen IP LLC; Moshe Pinchas

(57) ABSTRACT

Provided are acidic thermophilic polygalacturonase TePG28A, encoding gene and application thereof. The amino acid sequence thereof is as shown in SEQ ID NO. 1 or SEQ ID NO. 2. The expressed acidic thermophilic polygalacturonase by means of cloning has advantages such as high enzyme activity and high stability; can adapt to the high temperature environment in the industrial production; has better application prospect; and can effectively degrade pectic substances such as polygalacturonic acid and pectin; and can be effectively applied to the industrial field of feed, food, and textile, etc.

6 Claims, 2 Drawing Sheets
Specification includes a Sequence Listing.

ACIDIC THERMOPHILIC POLYGALACTURONASE TEPG28A, AND ENCODING GENE AND APPLICATION THEREOF

FIELD OF THE INVENTION

The present invention relates to the field of genetic engineering, particularly to an acidic thermophilic polygalacturonase TePG28A, encoding gene and application thereof.

BACKGROUND OF THE INVENTION

Cellulose, hemicellulose, pectin and a small amount of structural proteins are the main components of the plant cell wall. Pectinase is a general term of a series of enzymes that can degrade pectin. Polygalacturonase is the major enzyme cleaving the alpha-1,4-glycoside bond in the main chain of polygalacturonic acid of the water-soluble pectin. And, it is widely used in food, textile industrial fields, etc.

Polygalacturonase has been used in the feed field to eliminate the anti-nutritional effect of the pectin and improve the utilization rate of the feed. It has been applied to the field of food to improve the yield and clarity of the juice, and to the textile industry to enhance the wettability of cotton fibers and to reduce environmental pollution.

Therefore, it is meaningful to provide the polygalacturonases with the excellent properties since the applications of polygalacturonase in different industries depend on its different properties.

SUMMARY OF THE INVENTION

One order of the present invention is to provide an acidic thermophilic polygalacturonase TePG28A.

Another order of the present invention is to provide a gene encoding the above acidic thermophilic polygalacturonase TePG28A.

Another order of the present invention is to provide a recombinant vector comprising the above gene.

Another order of the present invention is to provide a recombinant cell comprising the above gene.

Another order of the present invention is to provide a method of preparing above acidic thermophilic polygalacturonase.

Another order of the present invention is to provide a use of the above acidic thermophilic polygalacturonase.

Thus, in one aspect, the present invention provided a novel acidic thermophilic polygalacturonase which was separated from *Talaromyces emersonii* 12802. According to an embodiment of the present invention, was provided an acidic thermophilic polygalacturonase which is selected from:

(a) a polypeptide comprising the amino acids as shown in SEQ ID NO:1 or SEQ ID NO:2; or
(b) a polypeptide with polygalacturonase activity which is derived from SEQ ID NO:1 or SEQ ID NO:2 by substitution, deletion and/or insertion of one or more amino acid residues.

SEQ ID NO. 1:
MHTIQPLLTYGLAVGAVLSSAAPTAVEKRASCTFTDAASAMASKTACS

TITLNNIAVPAGTTLDLTGLTSGTRVIFEGTTTFGYQEWSGPLVSISG

TDITVQGASGSVLDGDGARWWDGQGSNGGKTKPKFFYAHSLDSSSITG

ITIKNSPVQVFSIQSNNLSLTDITVDDADGDTQGGHNTDAFDIGSSTY

ITITNANVHNQDDCIAVNSGENIIFTGGTCTGGHGLSIGSVGGRSDNT

VKNVTIEHSTVTNSQNGVRIKTVYGATGSVSEVTYSNIQMSGITNYGI

VIEQDYENGSPTGTPTNGVPITDLTLNTVTGSVSSGATEIYILCGSGS

CSSWTWTGVSITGGSKSTKCENVPSGVSC

According to an embodiment of the present invention, said polygalacturonase comprises 365 amino acids with a signal peptide of 21 amino acids in N-terminal, as set in forth in SEQ ID NO:3.

SEQ ID NO. 3:
MHTIQPLLTYGLAVGAVLSSA

According to an embodiment of the present invention, the mature polygalacturonase protein comprised the amino acids as set forth in SEQ ID NO:2 having molecular weight of 35.2 kDa.

SEQ ID NO. 2:
APTAVEKRASCTFTDAASAMASKTACSTITLNNIAVPAGTTLDLTGLT

SGTRVIFEGTTTFGYQEWSGPLVSISGTDITVQGASGSVLDGDGARWW

DGQGSNGGKTKPKFFYAHSLDSSSITGITIKNSPVQVFSIQSNNLSLT

DITVDDADGDTQGGHNTDAFDIGSSTYITITNANVHNQDDCIAVNSGE

NIIFTGGTCTGGHGLSIGSVGGRSDNTVKNVTIEHSTVTNSQNGVRIK

TVYGATGSVSEVTYSNIQMSGITNYGIVIEQDYENGSPTGTPTNGVPI

TDLTLNTVTGSVSSGATEIYILCGSGSCSSWTWTGVSITGGSKSTKCE

NVPSGVSC

Yet another aspect of the invention is a gene encoding the above polygalacturonase, with the following characteristics:
(a) encoding a polypeptide comprising the amino acids as shown in SEQ ID NO:1 or SEQ ID NO: 2;
(b) encoding a polypeptide with polygalacturonase activity which is derived from SEQ ID NO: 1 or SEQ ID NO: 2 by substitution, deletion and/or insertion of one or more amino acid residues.

Preferably, the gene encoding the above high-temperature acid polygalacturonase according to an embodiment of the present invention is selected from
(a) DNA comprising a nucleotide sequence set in forth in SEQ ID NO:4 or SEQ ID NO:6; or
(b) DNA hybridizing under stringent conditions to a nucleotide as set in forth in SEQ ID NO:4 or SEQ ID NO:6, and encoding a polypeptide with polygalacturonase activity.

Preferably, said gene has a nucleotide sequence set in forth in SEQ ID NO:4 in full length of 1095 bp.

SEQ ID NO. 4:
(SEQ ID NO. 4)
ATGCATACGATCCAACCTCTTCTAACCTATGGGCTGGCCGTGGGAGCT

GTCCTTTCCTCAGCGGCCCCAACTGCTGTCGAGAAGCGTGCCAGCTGC

ACCTTTACCGATGCTGCTTCTGCCATGGCAAGCAAGACAGCCTGCTCG

-continued

```
ACTATCACGCTGAACAACATTGCCGTTCCTGCTGGGACCACCTTGGAC
CTGACGGGCTTGACATCCGGCACCAGGGTCATCTTCGAAGGAACAACC
ACCTTTGGATACCAGGAATGGAGCGGTCCCCTGGTTTCTATCTCCGGC
ACCGATATTACCGTTCAGGGTGCTTCGGGCTCCGTGCTTGACGGTGAC
GGTGCCCGCTGGTGGGATGGACAGGGCAGCAATGGCGGCAAGACCAAG
CCCAAGTTCTTCTACGCCCATAGCTTGGACTCTTCGTCCATCACTGGC
ATTACTATCAAGAACTCCCCTGTTCAAGTCTTCAGCATCCAGTCCAAC
AATTTGAGCCTGACGGATATCACCGTCGATGACGCCGATGGCGACACC
CAAGGCGGCCACAATACCGACGCCTTTGATATCGGTAGCTCCACTTAT
ATCACGATCACGAACGCTAATGTTCACAATCAGGATGACTGCATTGCA
GTCAACTCAGGGGAGAACATCATCTTCACTGGCGGCACCTGCACCGGC
GGCCACGGTCTCTCCATCGGCTCTGTCGGCGGCCGCTCAGACAACACC
GTCAAGAACGTCACCATCGAGCACTCCACCGTGACCAACTCCCAGAAT
GGCGTGCGTATCAAGACCGTGTACGGCGCGACCGGCTCCGTCTCCGAA
GTCACTTACTCCAACATCCAAATGTCTGGAATCACGAACTATGGCATC
GTGATCGAGCAGGACTACGAGAACGGCAGCCCAACTGGTACCCCGACA
AACGGTGTCCCTATTACAGATCTCACTCTCAATACTGTGACTGGTAGC
GTTTCGAGTGGTGCTACGGAGATTTACATTCTCTGCGGATCTGGAAGC
TGCTCTAGTTGGACTTGGACGGGTGTTTCAATTACTGGTGGCTCGAAG
AGCACTAAATGTGAGAATGTGCCTTCTGGAGTTTCTTGC.
```

According to an embodiment of the present invention, the gene encoding polygalacturonase isolated by PCR method comprises a nucleotide sequence set in forth in SEQ ID NO:5 coding a signal peptide.

(SEQ ID NO. 5)
```
ATGCATACGATCCAACCTCTTCTAACCTATGGGCTGGCCGTGGGAGCT
GTCCTTTCCTCAGCG.
```

A gene encoding a mature polygalacturonase had a nucleotide sequence set in forth in SEQ ID NO:6.

SEQ ID NO. 6
```
GCCCCAACTGCTGTCGAGAAGCGTGCCAGCTGCACCTTTACCGATGCT
GCTTCTGCCATGGCAAGCAAGACAGCCTGCTCGACTATCACGCTGAAC
AACATTGCCGTTCCTGCTGGGACCACCTTGGACCTGACGGGCTTGACA
TCCGGCACCAGGGTCATCTTCGAAGGAACAACCACCTTTGGATACCAG
GAATGGAGCGGTCCCCTGGTTTCTATCTCCGGCACCGATATTACCGTT
CAGGGTGCTTCGGGCTCCGTGCTTGACGGTGACGGTGCCCGCTGGTGG
GATGGACAGGGCAGCAATGGCGGCAAGACCAAGCCCAAGTTCTTCTAC
GCCCATAGCTTGGACTCTTCGTCCATCACTGGCATTACTATCAAGAAC
TCCCCTGTTCAAGTCTTCAGCATCCAGTCCAACAATTTGAGCCTGACG
GATATCACCGTCGATGACGCCGATGGCGACACCCAAGGCGGCCACAAT
ACCGACGCCTTTGATATCGGTAGCTCCACTTATATCACGATCACGAAC
GCTAATGTTCACAATCAGGATGACTGCATTGCAGTCAACTCAGGGGAG
AACATCATCTTCACTGGCGGCACCTGCACCGGCGGCCACGGTCTCTCC
ATCGGCTCTGTCGGCGGCCGCTCAGACAACACCGTCAAGAACGTCACC
ATCGAGCACTCCACCGTGACCAACTCCCAGAATGGCGTGCGTATCAAG
ACCGTGTACGGCGCGACCGGCTCCGTCTCCGAAGTCACTTACTCCAAC
ATCCAAATGTCTGGAATCACGAACTATGGCATCGTGATCGAGCAGGAC
TACGAGAACGGCAGCCCAACTGGTACCCCGACAAACGGTGTCCCTATT
ACAGATCTCACTCTCAATACTGTGACTGGTAGCGTTTCGAGTGGTGCT
ACGGAGATTTACATTCTCTGCGGATCTGGAAGCTGCTCTAGTTGGACT
TGGACGGGTGTTTCAATTACTGGTGGCTCGAAGAGCACTAAATGTGAG
AATGTGCCTTCTGGAGTTTCTTGC
```

In yet another embodiment, the present invention relates to a recombinant vector comprising said polynucleotide encoding the above polygalacturonase.

In yet another embodiment, the present invention relates to a recombinant host cell comprising said polynucleotide encoding the above polygalacturonase. In a preferred embodiment, said recombinant host cell was strain GS115/TePG28A.

The present invention relates to a method of producing polygalacturonase comprising the steps of:

(1) transforming a host cell with the DNA construct or a recombinant vector of comprising said polynucleotide encoding the above polygalacturonase to obtain the recombinant host cell;

(2) cultivating the recombinant host cell to induce the expression of polygalacturonase; and (3) isolating and recovering said polygalacturonase.

Yet another aspect of the invention is the application of said polygalacturonase, especially to energy sources, food, textile or feed fields.

According to the embodiment of the present invention, gene cloned by PCR from *Talaromyces emersonii* 12802 was identified as a novel gene by BLAST. Therefore, the amino acid sequence of ORF from *Talaromyces emersonii* 12802 was named TePG28A.

According to the embodiment of the present invention, "polygalacturonase", as used herein, referred to an isolated protein comprising the amino acid sequence depicted in SEQ ID NO: 1 or SEQ ID NO:2. In another embodiment, "polygalacturonase", as used herein, referred to a derivate of said protein, which is obtainable from SEQ ID NO: 1 or SEQ ID NO:2 by substitution, deletion and/or insertion of one or more (e.g., one or several, or a value selected from 1-10, e.g., 1, 2, 3, 4, 5, 6, 7, 8, 9 or 10, or ranges intermediated to the above-recited values) amino acid residues, and maintains the polygalacturonase activity. For example, a common strategy is conservative amino acid substitutions that the amino acid residue is replaced with an amino acid residue having a similar side chain without effect on the activity of the polygalacturonase. Families of amino acid residues having similar side chains have been defined in the art.

Furthermore, it is well known in the art that during the cloning of genes, usually enzyme recognition sites are designed, which would result in one or several non-relating amino acid residues on the ends of target protein without affecting the activity thereof.

According to the embodiment of the present invention, in order to construct a fusion protein, to enhance expression of recombinant protein, to obtain an recombinant protein automatically secreted outside the host cell, or to aid in the purification of the recombinant protein, suitable peptide linker, signal peptide, leader peptide, terminal extensions, glutathione S-transferase (GST), maltose E binding protein, protein A, tags such as 6His or Flag, or proteolytic cleavage site for Factor Xa, thrombin or enterokinase are usually introduced into the N- or C-terminus of the recombinant protein or within other suitable regions in the proteins.

In another embodiment, the protein with polygalacturonase activity according to the present invention comprises an amino acid sequence which is encoded by a nucleotide sequence which hybridizes under stringent conditions to a nucleotide sequence as set forth SEQ ID NO: 4 or SEQ ID NO: 6. As used herein, the term "hybridizes under stringent conditions" is intended to describe conditions for hybridization and washing under which nucleotide sequence at least 65% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to one of the ordinary skills in the art and can be found in *Current Protocols in Molecular Biology*, John Wiley & Sons, N.Y. (1989), 6.3.1-6.3.6. A preferred, non-limiting example of stringent hybridization conditions is hybridization in 6× sodium chloride/sodium citrate (SSC) at about 45° C., followed by one or more washes in 0.2×SSC, 0.1% SDS at 50-65° C. A person skilled in the art understands that high stringent condition could be realized by raising the hybridization temperature up to 50° C., 55° C., 60° C. or 65° C.

Besides, it will be appreciated by one of the ordinary skills in the art that genetic polymorphism due to natural variation may exist among individuals within a population. Such natural variations can typically result in 1-5% variance in the nucleotide sequence of the gene encoding the polygalacturonase. Any and all such nucleotide variations and resulting amino acid polymorphisms in polygalacturonase that are the result of natural variation and that do not alter the functional activity of polygalacturonase proteins are intended to be within the scope of the invention. Therefore, the present invention also encompasses a polypeptide with polygalacturonase activity encoded by such an allele or natural variant of the polynucleotide as shown in SEQ ID NO: 4 or SEQ ID NO:6.

In a preferred embodiment, a polygalacturonase protein is such an active protein that is at least about 60%, 61%, 62%, 63%, 64%, 65%, 66%, 67%, 68%, 69%, or at least about 70%, 71%, 72%, 73%, 74%, 75%, 76%, 77%, 78%, 79%, or at least about 80%, 81%, 82%, 83%, 84%, 85%, 86%, 87%, 88%, 89%, or at least about 90%, 91%, 92%, 93%, 94%, 95%, 96%, 97%, 98%, more preferably at least about 98.1%, 98.2%, 98.3%, 98.4%, 98.5%, 98.6%, 98.7%, 98.8%, 98.9%, and even more preferably at least about 99%, 99.1%, 99.2%, 99.3%, 99.4%, 99.5%, 99.6%, 99.7%, 99.8%, 99.9% or more homologous to the entire amino acid sequence as shown in SEQ ID NO: 1 or SEQ ID NO:2. Ranges and identity values intermediated to the above-recited values (e.g., 60-90% homologous or 98.1-99.9% identical) are also intended to be included in the present invention.

On the other hand, the present invention provides a novel polygalacturonase gene of SEQ ID NO:4 or SEQ ID NO:6. The invention further encompasses nucleic acid molecules that differ from one of the nucleotide sequences depicted in SEQ ID NO:4 or SEQ ID NO:6 of the invention due to degeneracy of the genetic code and thus encode the same polygalacturonase protein. In another embodiment, an isolated nucleic acid molecule of the invention is a nucleotide sequence which hybridizes under stringent conditions, to a nucleotide sequence of SEQ ID NO:4 or SEQ ID NO:6, preferably is the allele or natural variant thereof.

In a still further embodiment, the nucleic acid molecule of the invention encodes a full length polygalacturonase protein which is substantially homologous to an amino acid sequence of SEQ ID NO:1 or SEQ ID NO:2 for example, a protein that derived from SEQ ID NO: 1 or SEQ ID NO:2 by substitution, deletion and/or insertion of one or more (e.g., one or several, or a value selected from 1-10) amino acid residues, or one that is at least 99% homologous to the amino acid sequence of SEQ ID NO:1 or SEQ ID NO:2. Such a nucleic acid molecule is preferably at least about 60%, 61%, 62%, 63%, 64%, 65%, 66%, 67%, 68%, 69%, or at least about 70%, 71%, 72%, 73%, 74%, 75%, 76%, 77%, 78%, 79%, or at least about 80%, 81%, 82%, 83%, 84%, 85%, 86%, 87%, 88%, 89%, more preferably at least about 90%, 91%, 92%, 93%, 94%, 95%, 96%, 97%, 97.7%, 97.8%, 97.9%, or at least about 98%, 98.1%, 98.2%, 98.3%, 98.4%, 98.5%, 98.6%, 98.7%, 98.8%, 98.9%, and even more preferably at least about 99%, 99.1%, 99.2%, 99.3%, 99.4%, 99.5%, 99.6%, 99.7%, 99.8%, 99.9% or more homologous to a nucleotide sequence of SEQ ID NO:4 or SEQ ID NO:6. Ranges and identity values intermediate to the above-recited values (e.g., 76-97% homologous or 97.8-99.9% identical) are also intended to be included in the present invention.

The recombinant expression vectors of the invention can be designed for expression of polygalacturonase proteins in prokaryotic or eukaryotic cells. For example, polygalacturonase gene can be expressed in bacterial cells such as *E. coli*, yeast such as *Pichia* or *Aspergillus*, insect cells such as Sf9 cell or silkworm cell using baculovirus expression vectors, or plant cell such as *Arabidopsis*, tobacco, corn, and so on, mediated by *Agrobacterium tumefaciens*. Thus, the invention pertains to host cells into which a recombinant expression vector of the invention has been introduced, with *Pichia* preferred. *Pichia pastoris* is a methylotrophic yeast, capable of metabolizing methanol as its sole carbon source. This system is well-known for its ability to express high levels of heterologous proteins. As an effective expression system, many of polygalacturonase gene have successfully expressed in *P. pastoris*. The novel polygalacturonase gene also expressed in *P. pastoris* and had high levels of expression. So it will be very easy to mass-produce the polygalacturonase by fermentation, and the cost will be lower than ever.

Vector DNA can be introduced into prokaryotic or eukaryotic cells via conventional transformation or transfection techniques. A host cell of the invention, such as a prokaryotic or eukaryotic host cell in culture, can be used to produce (i.e., express) a polygalacturonase protein. Accordingly, the invention further provides methods for producing polygalacturonase proteins using the host cells of the invention. In one embodiment, the method comprises culturing the host cell into which a recombinant expression vector encoding a polygalacturonase protein has been introduced, or into which genome has been introduced a gene encoding a wild-type or altered polygalacturonase protein in a suitable medium until polygalacturonase protein is produced. In another embodiment, the method further comprises isolating polygalacturonase proteins from the medium or the host cell.

With the aim to solve the requirement of the polygalacturonase with the improved properties applied to feed, wine, juice, bread, and paper industries, we had isolated a novel polygalacturonase from *Talaromyces emersonii* 12802. The polygalacturonase had several advantages of being very stable between pH 2.0 and pH 7.0 and the optimal pH of 4.5, maintaining 90% of the activity at 60° C. for 1 h, and the optimal temperature of 70° C., and having enzyme activity of 41,786 U/mg. Therefore, the polygalacturonase of the present invention is thermostable and acid stable, and can be applied to effectively hydrolyzing polygalacturonic acid and pectin at higher temperature during the production in feed, food and textile fields.

BRIEF DESCRIPTIONS OF THE DRAWINGS

EXAMPLES

Figure 1:
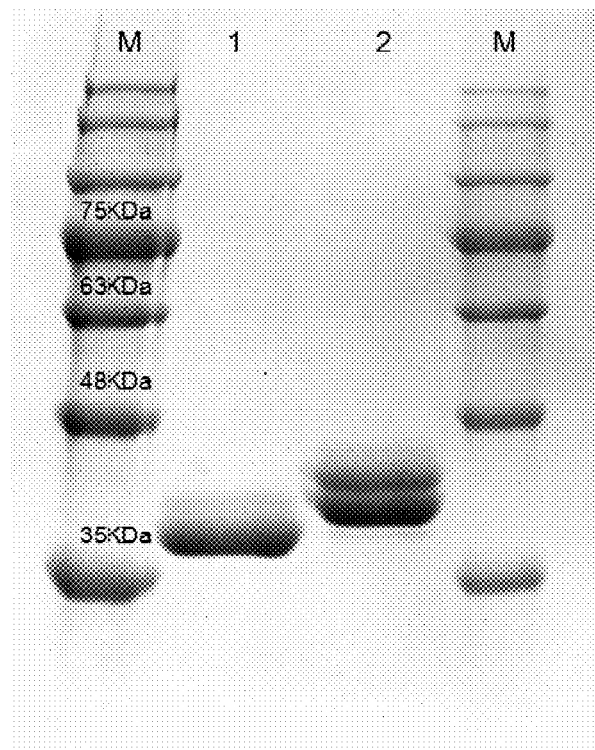
FIG. 1 shows the expression and deglycosylation of the recombinant polygalacturonase, wherein 1: purified and deglycosylated TePG28A protein, and 2: only purified TePG28A protein.

The present invention is further illustrated with reference to the following Examples and the appended drawings, which should by no means be construed as limitations of the present invention.

Test Materials and Reagents

1. Strains and vectors: *Talaromyces emersonii* 12802; *Pichia pastoris* strain GS115 (Invitrogen); and vetor pPIC9 (Invitrogen, San Diego, Calif.).

2. Enzymes and other biochemical reagents: restriction endonucleases (TaKaRa); ligase (Invitrogen); and birch xylan (Sigma)

3. Medium:
(1) taking potato dextrose medium as *Talaromyces emersonii* 12802 Medium, including 1000 mL of potato juice, 10 g of dextrose, and 25 g of arga, natural pH.
(2) *E. coli.* LB medium: 1% of peptone, 0.5% of yeast extract, and 1% of NaCl, natural pH.
(3) BMGY medium: 1% of yeast extract; 2% of peptone; 1.34% of YNB, 0.00004% of Biotin; and 1% of glycerol (V/V).
(4) BMMY medium: 1% of yeast extract; 2% of peptone; 1.34% of YNB, 0.00004% of Biotin; and 0.5% of methanol (V/V).

Suitable biology laboratory methods not particularly mentioned in the examples as below can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other kit laboratory manuals.

Example 1 Cloning Polygalacturonase Gene TePG28A from *Talaromyces emersonii* 12802

Total RNA is isolated from *Talaromyces emersonii* 12802 having been induced for 3 days. It was possible to design a pair of degenerate primers to amplify part fragment of the polygalacturonase gene based on the conserved fragment of the family 3 of polygalacturonase from the *Talaromyces emersonii* 12802 DNA by RT-PCR.

P1:
(SEQ ID NO. 7)
5'-GACTACGTAGCCCCAACTGCTGTCGAGAAGCGTG -3';

P2:
(SEQ ID NO. 8)
5'- GTCGAATTCCTAGCAAGAAACTCCAGAAGGCACATTCTCAC -3'.

PCR amplification was performed by optimizing PCR parameters as follows: degenerating at 95° C. for 5 minutes, followed by 30 cycles at: degenerating at 94° C. for 30 seconds/annealing temperature at 60° C. for 30 seconds/extending at 72° C. for 1 minute, and a final extension of 10 minutes at 72° C. PCR product comprising 1000 bp was obtained and linked to vector pEASY-T3 for sequencing. Two flanking sequences were obtained, and assembled into polygalacturonase gene with 1095 bp in full length coding 365 amino acids including a terminal. The mature protein encoded by this gene has molecular weight of 35.2 kDa.

Example 2 Producing Recombinant Polygalacturonase

The coding region of mature protein was amplified. The DNA purified was inserted into pPIC9 at the EcoRI and SnaB sites, as described by the manufacturer instruction to obtain DNA construct pPIC-PG5804. The construct was transformed into *Pichia pastoris* strain GS115 to obtain the recombinant cell GS115/TePG28A.

The expression vector comprising the full-length gene enconding polygalacturonase was constructed and transformed to *Pichia pastoris* strain GS115 by the same method as above.

The transformed *Pichia pastoris* strain GS115 (Invitrogen) were incubated in 300 mL of BMGY for 48 h at 30° C. and 250 rpm, and then the cells were spun down and suspended in 150 mL of BMMY to induce the polygalacturonase gene expression. 72 hours after induction, the supernatant was recovered by spinning to test the activity of the polygalacturonase. The enzyme activity of the purified recombinant polygalacturonase was 41,786 U/mg.

Example 4 Measuring the Properties of the Recombinant Polygalacturonase

900 µl of substrate solution of polygalacturonic acid in concentration of 0.33% was added to 100 µL of diluted enzyme solution, which was reacted at 70° C. and pH 3.5 for 10 minutes. Then, 1.5 mL of DNS was added to stop the reaction. OD540 was measured.

1 unit of polygalacturonase activity was determined to be the enzyme amount releasing 1 µmol of reducing sugar by decomposing substrate for 1 minute.

Example 5 Measuring the Properties of the Recombinant Polygalacturonase TePG28A

1. Optimum pH Values and pH Stability

Figure 2:
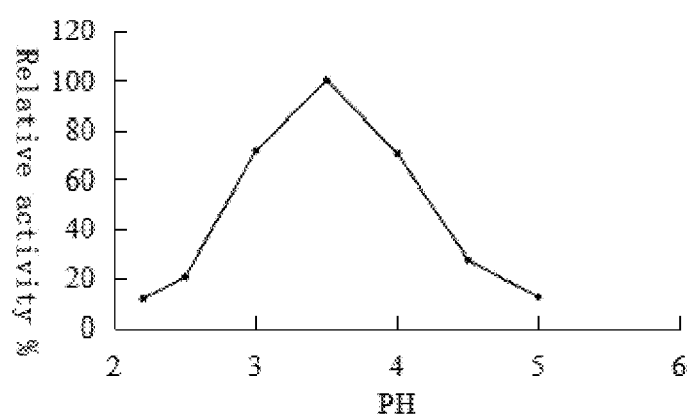
FIG. 2 shows optimum pH values for the recombinant polygalacturonase TePG28A.
Figure 3:
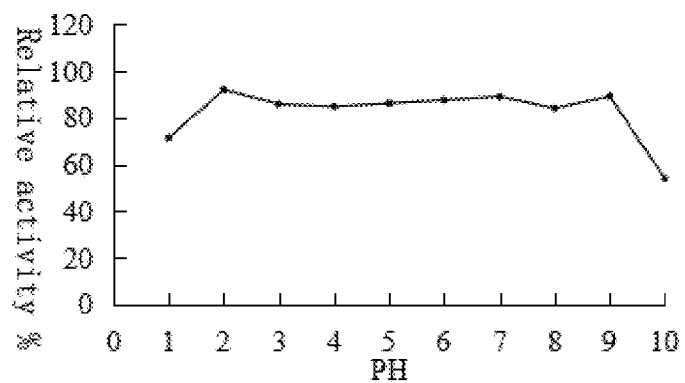
FIG. 3 shows pH stabilities for the recombinant polygalacturonase TePG28A.

The polygalacturonase purified in example 4 was reacted in the different pH to determine optimum pH. The activity of polygalacturonase was measured using polygalacturonic acid as substrate in 0.1 mol/L citric acid-sodium dimetallic phosphate buffer with different pH at 70° C. As is shown in FIG. 2, the activity of the recombinant polygalacturonase varied with pH. The highest activity was observed at pH 3.5. The recombinant polygalacturonase was maintained at 37° C. at different pH for 60 min followed by measuring the activity in buffer with pH3.5 at 70° C. FIG. 3 showed the enzyme was stable at pH 1.0 to 7.0 and maintained 90% of activity after being treated for 60 min at pH 1.0 to 7.0.

2. Optimum Temperature and Heat Stability

Figure 4:
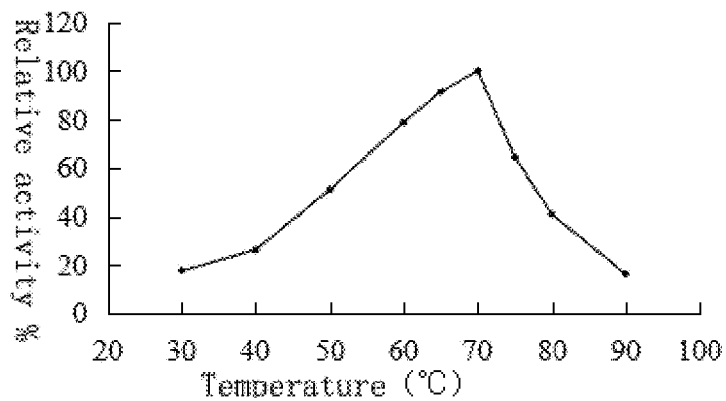
FIG. 4 shows optimum temperature values for the recombinant polygalacturonase TePG28A.
Figure 5:
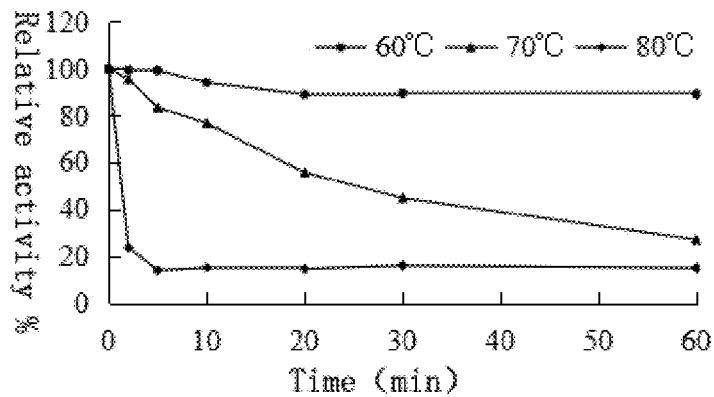
FIG. 5 shows heat stability for the recombinant polygalacturonase TePG28A.

The polygalacturonase was reacted in the different temperatures to determine optimum temperature. The activity of polygalacturonase was measured using polygalacturonic acid as substrate in citric acid-sodium dimetallic phosphate buffer (pH 4.0) at different temperatures. As shown in FIG. 4, the activity of polygalacturonase varied with temperatures. The highest activity was observed at 70° C. FIG. 4 showed the enzyme activity was thermalstable at 70° C., more than 90% of the enzyme activity was still maintained when the enzyme was maintained at 60° C. for 1 h.

The invention claimed is:

1. A method of producing a polygalacturonase having the amino acid sequence of SEQ ID NO: 1 or SEQ ID NO: 2, comprising the steps of:
   (1) transforming a prokaryotic or eukaryotic host cell in culture with a polynucleotide comprising a nucleotide sequence encoding said polygalacturonase to obtain a recombinant host cell;
   (2) cultivating the recombinant host cell to induce expression of said polygalacturonase; and
   (3) isolating and recovering said polygalacturonase.

2. A method of degrading polygalacturonic acid of a water-soluble pectin, comprising contacting said water-soluble pectin with an isolated or purified polygalacturonase having the amino acid sequence of SEQ ID NO: 1 or SEQ ID NO: 2, thereby degrading the polygalacturonic acid of said water-soluble pectin.

3. The method of claim 2, wherein the degrading of polygalacturonic acid of a water-soluble pectin is during production of a feed, food or textile.

4. The method of claim 2, wherein said polygalacturonase has an optimal pH of 4.5, an optimal temperature of 70° C., pH stability within pH 2.0 to pH 7.0 and[H] maintains 90% polygalacturonase activity at 60° C. for 1 hour.

5. The method of claim 2, wherein said polygalacturonase is produced by a recombinant host cell comprising a heterologous polynucleotide encoding said polygalacturonase.

6. The method of claim 5, wherein said heterologous polynucleotide has the nucleotide sequence of SEQ ID NO: 4 or SEQ ID NO: 6.

* * * * *

SEQUENCE LISTING

```
<160> NUMBER OF SEQ ID NOS: 8

<210> SEQ ID NO 1
<211> LENGTH: 365
<212> TYPE: PRT
<213> ORGANISM: Talaromyces emersonii

<400> SEQUENCE: 1

Met His Thr Ile Gln Pro Leu Leu Thr Tyr Gly Leu Ala Val Gly Ala
1               5                   10                  15

Val Leu Ser Ser Ala Ala Pro Thr Ala Val Glu Lys Arg Ala Ser Cys
            20                  25                  30

Thr Phe Thr Asp Ala Ala Ser Ala Met Ala Ser Lys Thr Ala Cys Ser
        35                  40                  45

Thr Ile Thr Leu Asn Asn Ile Ala Val Pro Ala Gly Thr Thr Leu Asp
    50                  55                  60

Leu Thr Gly Leu Thr Ser Gly Thr Arg Val Ile Phe Glu Gly Thr Thr
65                  70                  75                  80

Thr Phe Gly Tyr Gln Glu Trp Ser Gly Pro Leu Val Ser Ile Ser Gly
                85                  90                  95

Thr Asp Ile Thr Val Gln Gly Ala Ser Gly Ser Val Leu Asp Gly Asp
            100                 105                 110

Gly Ala Arg Trp Trp Asp Gly Gln Gly Ser Asn Gly Gly Lys Thr Lys
        115                 120                 125

Pro Lys Phe Phe Tyr Ala His Ser Leu Asp Ser Ser Ser Ile Thr Gly
    130                 135                 140

Ile Thr Ile Lys Asn Ser Pro Val Gln Val Phe Ser Ile Gln Ser Asn
145                 150                 155                 160

Asn Leu Ser Leu Thr Asp Ile Thr Val Asp Asp Ala Asp Gly Asp Thr
                165                 170                 175

Gln Gly Gly His Asn Thr Asp Ala Phe Asp Ile Gly Ser Ser Thr Tyr
            180                 185                 190

Ile Thr Ile Thr Asn Ala Asn Val His Asn Gln Asp Asp Cys Ile Ala
        195                 200                 205

Val Asn Ser Gly Glu Asn Ile Ile Phe Thr Gly Gly Thr Cys Thr Gly
    210                 215                 220

Gly His Gly Leu Ser Ile Gly Ser Val Gly Gly Arg Ser Asp Asn Thr
225                 230                 235                 240

Val Lys Asn Val Thr Ile Glu His Ser Thr Val Thr Asn Ser Gln Asn
                245                 250                 255

Gly Val Arg Ile Lys Thr Val Tyr Gly Ala Thr Gly Ser Val Ser Glu
            260                 265                 270

Val Thr Tyr Ser Asn Ile Gln Met Ser Gly Ile Thr Asn Tyr Gly Ile
        275                 280                 285

Val Ile Glu Gln Asp Tyr Glu Asn Gly Ser Pro Thr Gly Thr Pro Thr
    290                 295                 300

Asn Gly Val Pro Ile Thr Asp Leu Thr Leu Asn Thr Val Thr Gly Ser
305                 310                 315                 320
```

-continued

Val Ser Ser Gly Ala Thr Glu Ile Tyr Ile Leu Cys Gly Ser Gly Ser
                325             330             335

Cys Ser Ser Trp Thr Trp Thr Gly Val Ser Ile Thr Gly Gly Ser Lys
            340             345             350

Ser Thr Lys Cys Glu Asn Val Pro Ser Gly Val Ser Cys
        355             360             365

<210> SEQ ID NO 2
<211> LENGTH: 344
<212> TYPE: PRT
<213> ORGANISM: Talaromyces emersonii

<400> SEQUENCE: 2

Ala Pro Thr Ala Val Glu Lys Arg Ala Ser Cys Thr Phe Thr Asp Ala
1               5                   10                  15

Ala Ser Ala Met Ala Ser Lys Thr Ala Cys Ser Thr Ile Thr Leu Asn
            20                  25                  30

Asn Ile Ala Val Pro Ala Gly Thr Thr Leu Asp Leu Thr Gly Leu Thr
        35                  40                  45

Ser Gly Thr Arg Val Ile Phe Glu Gly Thr Thr Thr Phe Gly Tyr Gln
    50                  55                  60

Glu Trp Ser Gly Pro Leu Val Ser Ile Ser Gly Thr Asp Ile Thr Val
65                  70                  75                  80

Gln Gly Ala Ser Gly Ser Val Leu Asp Gly Asp Gly Ala Arg Trp Trp
                85                  90                  95

Asp Gly Gln Gly Ser Asn Gly Gly Lys Thr Lys Pro Lys Phe Phe Tyr
            100                 105                 110

Ala His Ser Leu Asp Ser Ser Ile Thr Gly Ile Thr Ile Lys Asn
        115                 120                 125

Ser Pro Val Gln Val Phe Ser Ile Gln Ser Asn Asn Leu Ser Leu Thr
    130                 135                 140

Asp Ile Thr Val Asp Asp Ala Asp Gly Asp Thr Gln Gly Gly His Asn
145                 150                 155                 160

Thr Asp Ala Phe Asp Ile Gly Ser Ser Thr Tyr Ile Thr Ile Thr Asn
                165                 170                 175

Ala Asn Val His Asn Gln Asp Asp Cys Ile Ala Val Asn Ser Gly Glu
            180                 185                 190

Asn Ile Ile Phe Thr Gly Gly Thr Cys Thr Gly Gly His Gly Leu Ser
        195                 200                 205

Ile Gly Ser Val Gly Gly Arg Ser Asp Asn Thr Val Lys Asn Val Thr
    210                 215                 220

Ile Glu His Ser Thr Val Thr Asn Ser Gln Asn Gly Val Arg Ile Lys
225                 230                 235                 240

Thr Val Tyr Gly Ala Thr Gly Ser Val Ser Glu Val Thr Tyr Ser Asn
                245                 250                 255

Ile Gln Met Ser Gly Ile Thr Asn Tyr Gly Ile Val Ile Glu Gln Asp
            260                 265                 270

Tyr Glu Asn Gly Ser Pro Thr Gly Pro Thr Asn Gly Val Pro Ile
        275                 280                 285

Thr Asp Leu Thr Leu Asn Thr Val Thr Gly Ser Val Ser Ser Gly Ala
    290                 295                 300

Thr Glu Ile Tyr Ile Leu Cys Gly Ser Gly Ser Cys Ser Ser Trp Thr
305                 310                 315                 320

Trp Thr Gly Val Ser Ile Thr Gly Gly Ser Lys Ser Thr Lys Cys Glu
                325                 330                 335

Asn Val Pro Ser Gly Val Ser Cys
            340

<210> SEQ ID NO 3
<211> LENGTH: 21
<212> TYPE: PRT
<213> ORGANISM: Talaromyces emersonii 12802

<400> SEQUENCE: 3

Met His Thr Ile Gln Pro Leu Leu Thr Tyr Gly Leu Ala Val Gly Ala
1               5                   10                  15

Val Leu Ser Ser Ala
            20

<210> SEQ ID NO 4
<211> LENGTH: 1095
<212> TYPE: DNA
<213> ORGANISM: Talaromyces emersonii

<400> SEQUENCE: 4

```
atgcatacga tccaacctct tctaacctat gggctggccg tgggagctgt cctttcctca      60
gcggccccaa ctgctgtcga gaagcgtgcc agctgcacct ttaccgatgc tgcttctgcc     120
atggcaagca agacagcctg ctcgactatc acgctgaaca acattgccgt tcctgctggg     180
accaccttgg acctgacggg cttgacatcc ggcaccaggg tcatcttcga aggaacaacc     240
acctttggat accaggaatg gagcggtccc ctggtttcta tctccggcac cgatattacc     300
gttcagggtg cttcgggctc cgtgcttgac ggtgacggtg cccgctggtg ggatggacag     360
ggcagcaatg gcggcaagac caagcccaag ttcttctacg cccatagctt ggactcttcg     420
tccatcactg gcattactat caagaactcc cctgttcaag tcttcagcat ccagtccaac     480
aatttgagcc tgacggatat caccgtcgat gacgccgatg cgacaccca aggcggccac     540 aataccgacg cctttgatat cggtagctcc acttatatca cgatcacgaa cgctaatgtt     600
cacaatcagg atgactgcat tgcagtcaac tcaggggaga acatcatctt cactggcggc     660
acctgcaccg gcggccacgg tctctccatc ggctctgtcg gcggccgctc agacaacacc     720
gtcaagaacg tcaccatcga gcactccacc gtgaccaact cccagaatgg cgtgcgtatc     780
aagaccgtgt acgcgcgac cggctccgtc tccgaagtca cttactccaa catccaaatg     840
tctggaatca cgaactatgg catcgtgatc gagcaggact acgagaacgg cagcccaact     900
ggtaccccga caaacggtgt ccctattaca gatctcactc tcaatactgt gactggtagc     960
gtttcgagtg gtgctacgga gatttacatt ctctgcggat ctggaagctg ctctagttgg    1020
acttggacgg gtgtttcaat tactggtggc tcgaagagca ctaaatgtga gaatgtgcct    1080
tctggagttt cttgc                                                    1095
```

<210> SEQ ID NO 5
<211> LENGTH: 63
<212> TYPE: DNA
<213> ORGANISM: Talaromyces emersonii 12802

<400> SEQUENCE: 5

```
atgcatacga tccaacctct tctaacctat gggctggccg tgggagctgt cctttcctca      60
gcg                                                                    63
```

<210> SEQ ID NO 6
<211> LENGTH: 1032

```
<212> TYPE: DNA
<213> ORGANISM: Talaromyces emersonii

<400> SEQUENCE: 6
gccccaactg ctgtcgagaa gcgtgccagc tgcacctttα ccgatgctgc ttctgccatg        60
gcaagcaaga cagcctgctc gactatcacg ctgaacaaca ttgccgttcc tgctgggacc       120
accttggacc tgacgggctt gacatccggc accagggtca tcttcgaagg aacaaccacc       180
tttggatacc aggaatggag cggtcccctg gtttctatct ccggcaccga tattaccgtt       240
cagggtgctt cgggctccgt gcttgacggt gacggtgccc gctggtggga tggacagggc       300
agcaatggcg gcaagaccaa gcccaagttc ttctacgccc atagcttgga ctcttcgtcc       360
atcactggca ttactatcaa gaactcccct gttcaagtct tcagcatcca gtccaacaat       420
ttgagcctga cggatatcac cgtcgatgac gccgatggcg acacccaagg cggccacaat       480
accgacgcct ttgatatcgg tagctccact tatatcacga tcacgaacgc taatgttcac       540
aatcaggatg actgcattgc agtcaactca ggggagaaca tcatcttcac tggcggcacc       600
tgcaccggcg gccacggtct ctccatcggc tctgtcggcg gccgctcaga caacaccgtc       660
aagaacgtca ccatcgagca ctccaccgtg accaactccc agaatggcgt gcgtatcaag       720
accgtgtacg gcgcgaccgg ctccgtctcc gaagtcactt actccaacat ccaaatgtct       780
ggaatcacga actatggcat cgtgatcgag caggactacg agaacggcag cccaactggt       840
accccgacaa acggtgtccc tattacagat ctcactctca atactgtgac tggtagcgtt       900
tcgagtggtg ctacggagat ttacattctc tgcggatctg gaagctgctc tagttggact       960 tggacggggtg tttcaattac tggtggctcg aagagcacta atgtgagaa tgtgccttct      1020 ggagtttctt gc                                                          1032

<210> SEQ ID NO 7
<211> LENGTH: 34
<212> TYPE: DNA
<213> ORGANISM: Artificial Sequence
<220> FEATURE:
<223> OTHER INFORMATION: synthesized primer

<400> SEQUENCE: 7
gactacgtag ccccaactgc tgtcgagaag cgtg                                    34

<210> SEQ ID NO 8
<211> LENGTH: 41
<212> TYPE: DNA
<213> ORGANISM: Artificial Sequence
<220> FEATURE:
<223> OTHER INFORMATION: synthesized primer

<400> SEQUENCE: 8
gtcgaattcc tagcaagaaa ctccagaagg cacattctca c                            41
```